US006290140B1

(12) United States Patent
Pesko et al.

(10) Patent No.: US 6,290,140 B1
(45) Date of Patent: Sep. 18, 2001

(54) ENERGY MANAGEMENT SYSTEM AND METHOD

(75) Inventors: Leonard B. Pesko, Phila, PA (US); Brian E. Gross, Clementon; Allan B. Gross, Cherry Hill, both of NJ (US); Robert N. Capper, Jr., Hardy, VA (US); Erich F. Kielburger, Philadelphia, PA (US)

(73) Assignee: EnergyIQ Systems, Inc., Deptford, NJ (US)

( * ) Notice: Subject to any disclaimer, the term of this patent is extended or adjusted under 35 U.S.C. 154(b) by 0 days.

(21) Appl. No.: 09/262,956

(22) Filed: Mar. 4, 1999

(51) Int. Cl.[7] .............................. A61F 11/06; G10K 11/00
(52) U.S. Cl. .............................. 236/47; 62/296; 181/175; 381/713
(58) Field of Search .............................. 236/47; 62/296; 381/71.3; 181/175; 415/119

(56) References Cited

U.S. PATENT DOCUMENTS 5,203,178 * 4/1993 Shyu .............................. 62/296 X
5,546,461 * 8/1996 Denenberg .............................. 381/71

* cited by examiner

*Primary Examiner*—William Wayner
(74) *Attorney, Agent, or Firm*—Caesar, Rivise, Bernstein, Cohen & Pokotilow, Ltd.

(57) ABSTRACT

A method is provided for managing the energy usage of an energy consuming system adapted to determine the energy of a controlled space, the energy consuming system including a plurality of operating components having on and off states and a plurality of differing noise levels when making transitions between the on and off states. The method includes determining the noise levels of the components of the energy consuming system, selecting a relatively low noise level component of the energy consuming system to provide a selected noise masking component, and causing a relatively high noise level component of the energy consuming system differing from the selected noise masking component to make a transition between on and off states. The method further includes causing the selected noise masking component to make a transition between its on and off states after the transition of high noise level component. The noise level of the selected noise masking component prior is increased prior to the transition of the high noise level component and decreased thereafter. The noise level of the selected noise masking component is gradually increased and gradually decreased. The operations are performed according to the occupancy of the controlled space. A parameter band of control is determined for controlling a selected parameter of the controlled space and the selected parameter of the controlled space is determined. A parameter drift of the selected parameter within the controlled space is determined in order to determine whether the parameter drift is adjusting the parameter toward the band of control. The energy of the controlled space is determined accordingly. Energy is applied to the energy system if the drift of the selected parameter of the controlled space is not adjusting the parameter toward the band of control.

25 Claims, 8 Drawing Sheets

ENERGY MANAGEMENT SYSTEM AND METHOD

BACKGROUND OF THE INVENTION

I. Field of the Invention

This invention relates to the field of energy management systems and, in particular, to the field of energy management systems for buildings having a plurality of individually controlled spaces.

II. Prior Art

During normal operation of an air conditioner air is forced over a coil while the air conditioner is in operation in order to permit the coil to absorb thermal energy from the air thereby cooling the air. However, it is also known in the prior art to continue to blow air over the coil after operation of the air conditioner terminates until the coil reaches ambient temperature. This decreases wasted energy.

SUMMARY OF THE INVENTION

The energy management system and method of the present invention manages energy usage by an energy consuming system The energy consuming system managed by management system and method of the present invention manages the energy consuming device by determining a plurality of parameters within the controlled space in order to reduce energy waste during heating and cooling of the controlled space. The controlled space can be one of a plurality of differing independently controllable spaces. For example, the controlled space can be a single room in a hotel wherein each such hotel room must be well controlled in order to avoid any periods of guest discomfort. Additionally, the control must be performed in a manner that does not cause any disturbance to an occupant of the controlled space.

For example, the present invention can determine the temperature settings of the controlled space as well as changes in temperature settings, or setbacks. Additionally, the hysteresis or span of the energy consuming device can be determined by the present invention. Furthermore, the energy management system of the present invention gives priority to the comfort of any occupants of the controlled space when controlling the energy usage of the controlled space since it is advantageously applied to buildings such as hotels where guest comfort is very important. The control logic of the system and method of the present invention can be applied to the various energy consuming devices of the controlled space on a priority basis.

The present invention can use parameters in addition to temperature settings in order to perform its control functions. For example, time of day, day of week, month, day of month, season of year, ingress and egress, window opening and closing, change in status, occupancy state, circadian rhythm of occupant, ambient noise level, light level, energy consumption, temperature drift rate and direction, rate of energy consumption, utility tariffs, humidity, and environment or weather can also be used in performing the control functions. The weather information can come, for example, from local weather instruments, data input, or the internet.

Additionally, by making use of card keys that can open a door of the controlled space it is possible to distinguish different types of individuals who enter the controlled space. For example, in a hotel it is possible to distinguish between guests and staff entering the controlled space according to the card key used. Therefore, occupant identification can also be used as system parameter in the present invention.

One way for the system of the present invention to increase the comfort level of the occupant of a controlled space is to reduce the perception of the noise coming from a heating, venting and air conditioning (HVAC) system. This is partly accomplished by reducing the frequency of the changes in the HVAC equipment noise levels. The frequency of the changes in HVAC noise levels can be reduced, for example, by increasing the control span of the energy consuming system managed by the system of the present invention.

Reduction of the noise perception of an occupant is also accomplished by reducing the changes in the noise levels of the HVAC equipment. The reduction in the changes in HVAC equipment noise level is obtained by masking the changes in noise levels created by on/off state transitions of the HVAC equipment. Masking the changes in noise level while the occupant is sleeping, and thereby reducing the noise perceived by the occupant, can cause the occupant to be awakened less frequently than with a standard on/off thermostatic control of the space.

The noise masking method of the present invention is effective to reduce the noise perceived by an occupant of the controlled space because individuals become accustomed to a constant level of ambient noise in a space they occupy. Noise sensitivity, or noise perception, by an individual can thus be related to the relative magnitude of changes in the ambient noise level once the individual becomes accustomed to a constant noise level. Greater changes in the noise level are more readily noticed by the individual than smaller ones.

Noise masking in accordance with the present invention can be advantageously performed any time that an occupant is present within the controlled space. Alternately, it can be performed only when the occupant is in the controlled space and is determined to be resting or sleeping. When the controlled space is unoccupied, or when the controlled space is occupied but the occupant is not resting or sleeping, the most energy efficient control method can take priority over noise reduction methods in order to reduce energy consumption.

In addition to providing further sleeping comfort using noise reduction, the method of the present invention enhances sleeping comfort using the natural circadian rhythm of the occupant. In this feature of the present invention changes in setback temperatures can be provided in accordance with the normal daily changes in the body temperature of the occupant. This feature of the present invention can also reduce energy consumption during occupied periods while adding to the comfort of the occupant and the ability of the occupant to sleep.

Additionally, the system and method of the present invention make use of ambient energy in controlling energy consumption within the controlled space. In order to perform this function the present invention is provided with an enthalpy system that can inhibit the use of any energy consuming devices. The enthalpy system inhibits the energy use when the measured natural direction of temperature change, or temperature drift, is the same as the desired direction of temperature change.

The system of the present invention determines the current natural direction of temperature change by repeatedly measuring the ambient temperature of the controlled space. This makes it possible to track the rate of temperature change as well as the direction of temperature change. If the natural direction of the ambient temperature change is the same as the desired direction, the system inhibits HVAC activation unless it is overridden by other predetermined conditions.

The determination to override the HVAC inhibit feature when the control direction and the natural direction are the same can be made according to many considerations. The considerations are mostly, but not exclusively, related to the comfort of the occupant. The override considerations can include occupancy of the controlled space, whether the occupant is in a rest or sleep state, the duration and rate of the ambient temperature change, and the time required to reach the desired temperature range using the natural temperature drift. Emergency conditions such as freezing and other predetermined emergencies can also be considered before inhibiting the HVAC equipment.

The system of the present invention establishes a band of control in addition to the span of control. The band of control can be selected to include or exclude the span of control and to extend predetermined amounts above and below the span of control. Furthermore, the band of control is determined by the logic of the energy management system of the present invention to save energy and to provide occupant comfort. When the controlled space is determined to be within the band of control no further energy is applied to the energy system unless an override condition exists.

Occupants of a controlled space can select heating or cooling of the controlled space. This is referred to as selecting the direction of control of the energy consuming system The system of the present invention can reverse the direction of control if necessary to satisfy a temperature setting. However, the direction of control can be reversed after satisfying the thermostatic requirements set by the span of control and temperature setpoint. Furthermore, the direction of control can be reversed if the temperature continues to drift until it reaches an override setting. This is considered an override situation because the energy consuming system is acting to satisfy defined override parameters. Energy savings are not necessarily maximized when this occurs.

When the controlled space is unoccupied the direction of control is selected by the system of the present invention. Under these conditions the HVAC equipment is only activated under the following circumstances. When the temperature is within a broad temperature control band defined by the system of the present invention no energy whatsoever is applied to the energy consuming system. If the temperature drifts either to the extreme upper limit or to the extreme lower limit of the control band either the heater or the air conditioner of the occupied space can be activated. The selection of the direction of the energy consuming device selected depends upon which direction is required to return the temperature of the controlled space to the limits defined by the band of control.

The system of the present invention may determine an out-of-limit condition exists and that the natural drift is in the direction required to return the measured temperature to the control band. Under these circumstances the present invention continues to inhibit energy use if no override or emergency conditions are detected. Heat pump use can be maximized since the system of the present invention always provides heat pump operation whenever the controlled space is unoccupied and whenever the controlled space is occupied but use of the heat pump does not cause occupant discomfort.

The system and method of the present invention permits real time based adaptive self programming in order to select setback levels and comfort settings within the occupied space. Additionally, the present invention manages energy usage based upon calendar and time information stored therein. This permits more accurate approximation of the amount of energy usage and the manner of energy usage within the controlled space. It also permits prediction of the expected energy requirements for heating and cooling the controlled space. For example, energy utilization parameters of a property, such as billing rates, demand rates, consumption rate, occupancy patterns, sleep, housekeeping, maintenance, outdoor temperature and humidity, usage of other energy devices such as lights, solar heat gains, and other parameters can be used by the present invention to manage the energy consuming device and control the environment of the controlled space. All of these parameters can have a calendar and time dependent variation.

BRIEF DESCRIPTION OF THE DRAWINGS

The features, objects, and advantages of the present invention will become more apparent from the detailed description set forth below when taken in conjunction with the drawings in which like reference characters identify corresponding elements throughout and wherein.

DETAILED DESCRIPTION OF THE INVENTION

Figure 1:
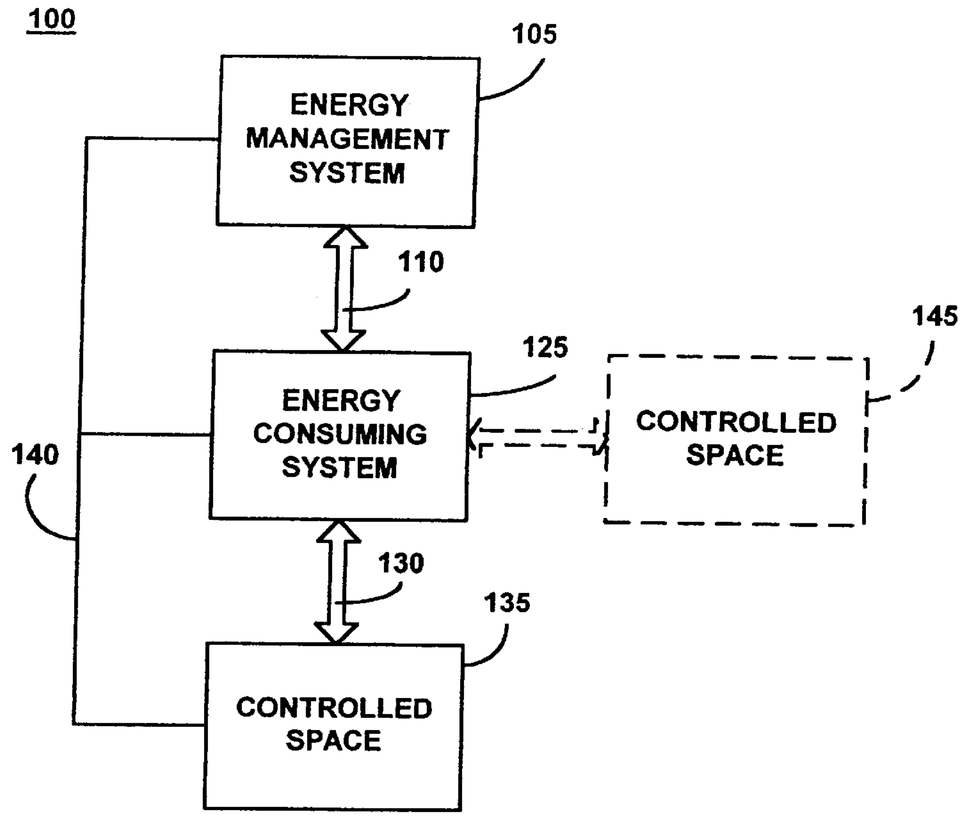
FIG. 1 shows a simplified block diagram of the energy management system of the present invention and a simplified block diagram of the energy consuming system managed by the energy management system of the present invention as well as the controlled space of the energy consuming system.
Figure 2A:
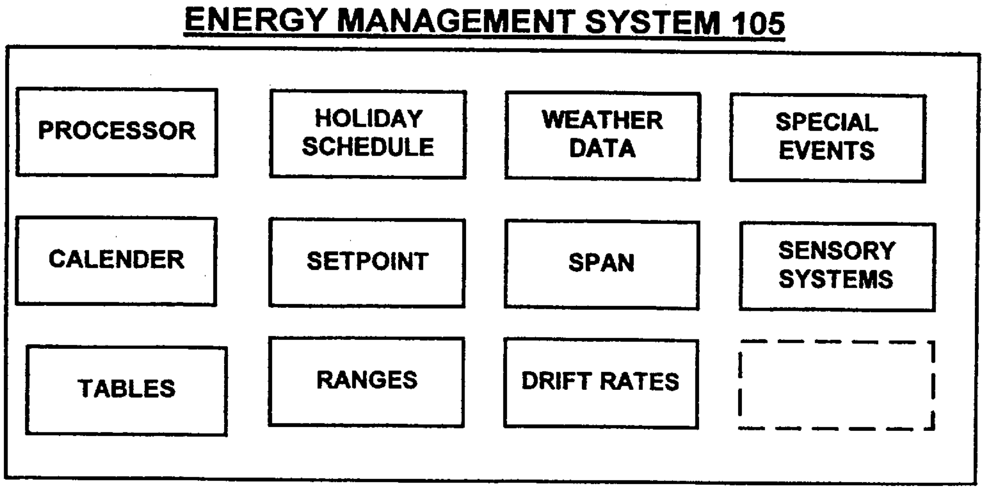
FIGS. 2A–C shows further details of the systems of FIG. 1.
Figure 2B:
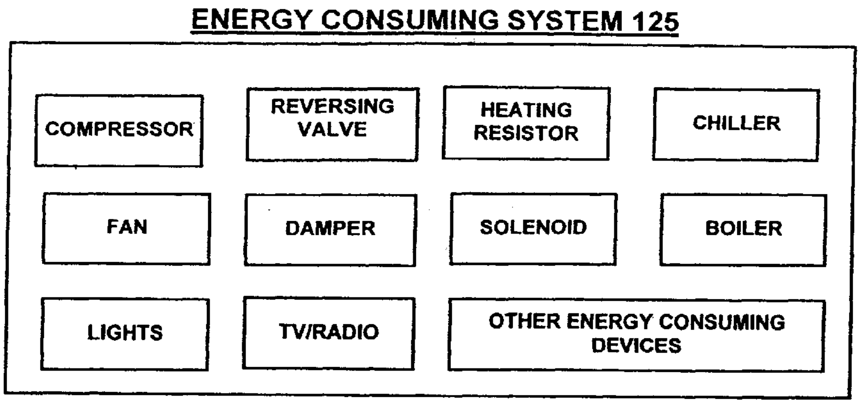
Figure 2C:
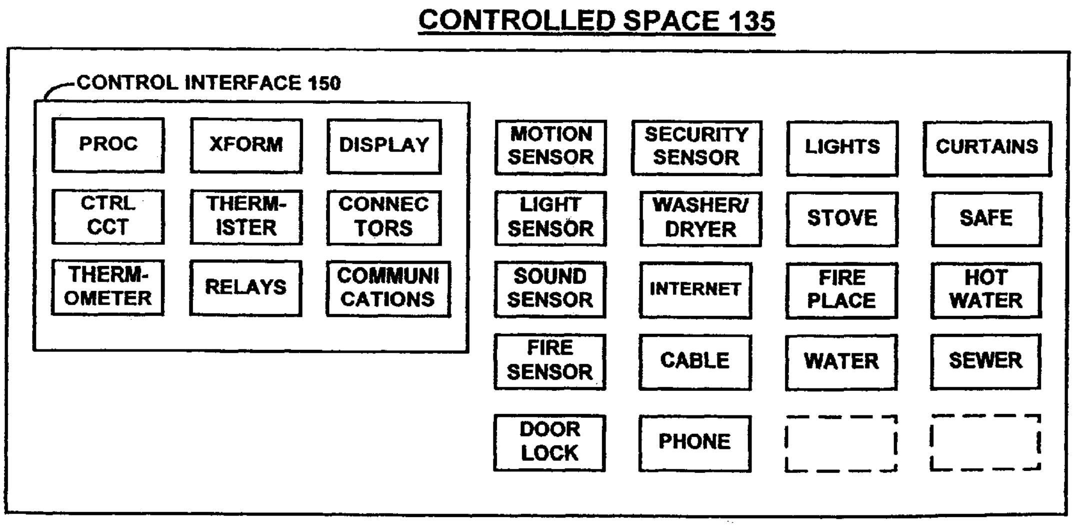

Referring now to FIGS. 1, 2A–C, there are shown simplfied block diagram 100 including energy management system 105 of the present invention as well as energy consuming system 125 and controlled space 135. FIGS. 1, 2A–C are greatly simplified for illustrative purposes. Energy management system 105 of the present invention can operate under the control of program code such as the program code set forth in a Software Appendix, attached hereto as Appendix I. The program code of Appendix I is provided in a form understandable to those skilled in the art.

Energy consuming system 125 consumes energy in order to control the environment of controlled space 135. Energy management system 105 controls controlled space 135 way of conduits 130. System 105 manages energy consuming system 125 while energy consuming system 125 controls the environment of controlled space 135 in a manner adapted to minimize the use of energy by energy consuming system 125 while maintaining a high comfort level for occupants of controlled space 135.

The management of energy consuming system 125 by energy management system 105 takes place by way of bidirectional communication bus 110. Bidirectional communication bus 110 can be multiplexed and can be used to transmit information such as coil temperature, inlet and outlet temperatures, air flow, and any system, network, or sensor information to energy management system 105. Energy management system 105 can also directly obtain information from controlled space 135 and directly control devices within controlled space 135 by way of bidirectional communication bus 140. Communication bus 140 can be multiplexed. Additionally, any electrical connections within conduits 130 can be multiplexed. The control lines of block diagram 100 can be 2-wire, 4-wire, or any other type of wiring suitable for communicating the required signals as well as wireless transmissions such as RF, IR, ultrasound or any other type of information transmission medium.

The information received by energy management system 105 can include room temperature, occupancy, door, window, alternate door, door lock identification, motion detected by infrared or ultrasound. The ingress/egress and identification information that obtained from the door lock information can be used to alert the system of the present invention to possible changes that must be responded to. Additionally, the information from the door lock can be used by the system of the present invention to actually begin a response in accordance with its programming. For example, fans and lights can be immediately controlled according to the door lock information. In order to perform these functions the system of the present invention must determine whether a door opening event represents an ingress or an egress. Occupancy information is used in making the ingress/egress determination.

Energy management system 105 can also obtain derived information and other system generated information. Furthermore, energy consuming system 125 can control the environment of a plurality of controlled spaces under the management of energy management system 105. For example, energy consuming system 125 can also control the environment of controlled space 145. All of the control interfaces of all of the various controlled spaces are individually addressable by energy management system 105.

The complexity of control interface 150 can vary widely. In the simplest case control interface 150 can include only a few electromechanical relays. Alternately, control interface 150 can contain sensors and a processor capable of performing all or part of the control of the environment of controlled space 135 without assistance from energy management system 105. In the latter case the processor in control interface 150 can continue to controlled space 135 in the event that energy management system 105 is inadvertently disconnected from the remainder of block diagram 100. This provides stopless operation in the event of malfunctions of this nature. The control exercised by the processor of control interface 150 can be limited. For example, the temperature of controlled space 135 can be maintained around a single setpoint.

In intermediate cases different amounts of processing power can be distributed between energy management system 105 and control interface 150. In these distributed processing cases the processor of control interface 150 can control, for example, an air conditioner, stoves, lights, and fireplaces. Some of the parameters or values that can be obtained by energy management system 105 and energy consuming system 125 in performing the functions of the present invention or can be used by energy management system 105 and energy consuming system 125 in performing the functions of the present invention are set forth as Appendix II.

Figure 3:
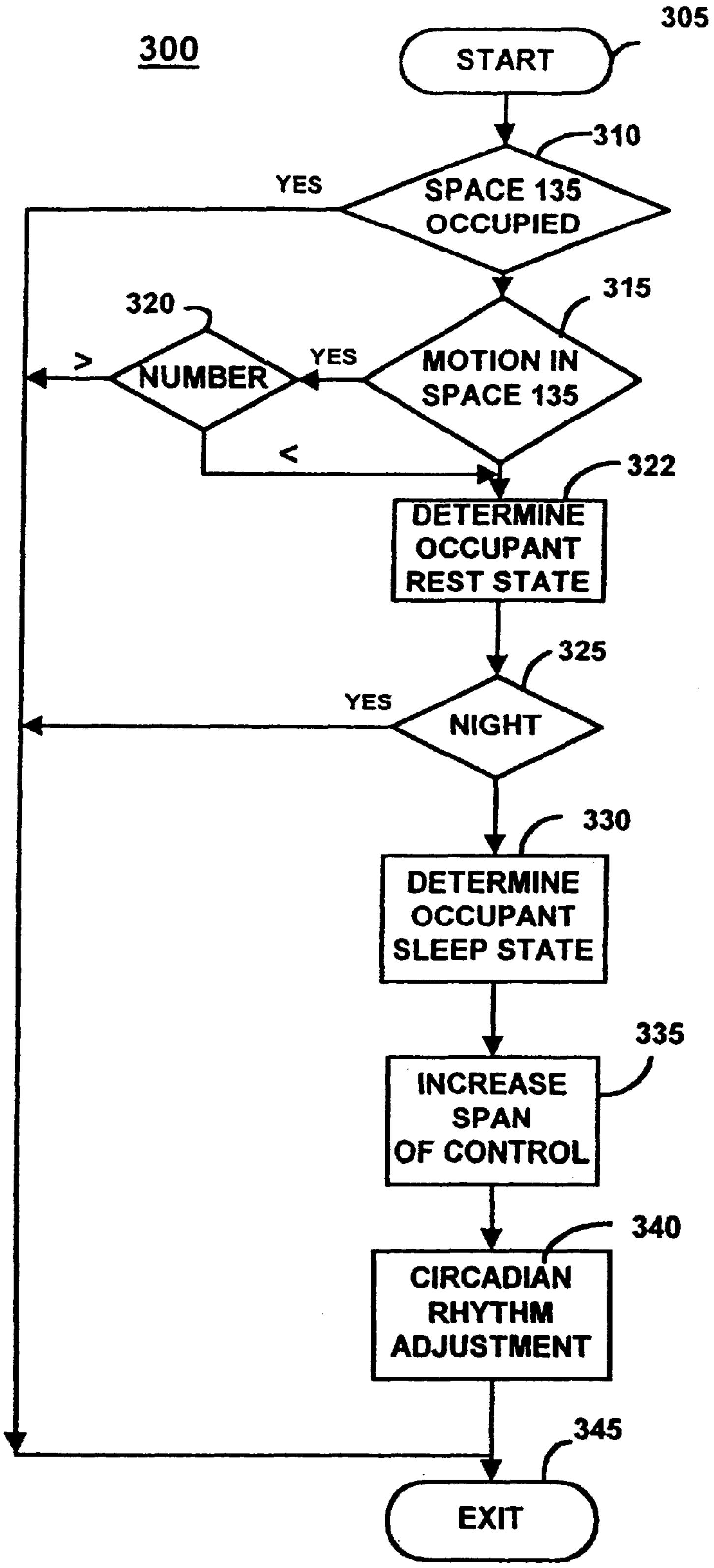
FIG. 3 shows a flow chart representation of an algorithm for determining occupant rest state and sleep state suitable for use with the energy management system and method of the present invention.

Referring now to FIG. 3, there is shown sleep determination algorithm 300 of the present invention. Sleep determination algorithm 300 sets forth a method for determining whether an occupant of controlled space 135 is resting or sleeping. This determination can be used to decide whether to perform predetermined operations in accordance with the method of the present invention. For example, noise reduction within controlled space 35 can be performed in accordance with the determinations of sleep determination algorithm 300.

Execution of sleep determination algorithm 300 begins at start terminal 305 and proceeds to decision 310 where a determination is made whether controlled space 135 is occupied. If controlled space 135 is not occupied execution of sleep determination algorithm 300 proceeds to exit terminal 345 and terminates. If controlled space 135 is occupied execution proceeds to decision 315. In decision 315 a determination is made whether motion has been detected within controlled space 135 during a predetermined period of time selected by the installer of the present invention. If no motion is detected during the selected period of time an assumption can be made that the occupant is resting as shown in block 322.

If motion is detected execution of sleep determination algorithm 300 proceeds to decision 320. In this embodiment of the invention the installer can allow for the fact that the occupant of controlled space 135 sometimes moves while sleeping. In order to allow for this an affirmative determination that the occupant is resting can be made at decision 320 for a small nonzero number of movements during the predetermined time period. The number of movements allowed for an affirmative determination of decision 320 can be adjusted within sleep determination algorithm 300 according to any of the parameters available to the system of the present invention.

If the resting determination is made in block 322 execution of sleep determination algorithm 300 proceeds to decision 325 where a determination is made whether sleep determination algorithm 300 is being executed during a night. The installer of the present invention can select any reference time of day that may seem appropriate for this determination. For example, it can be determined that a lack of motion after 10:00 PM is likely to indicate that the occupant is asleep. In an alternate embodiment of the invention the installer can permit sleep to be determined whenever there is little or no motion in an occupied space, regardless of the time of day.

If the determination of decision 325 is affirmative sleep determination algorithm 300 can determine that the occupant is asleep as set forth in block 330. In one preferred embodiment of energy management system 105 the control span of controlled space 135 can be increased when the occupant is determined to be asleep as set forth in block 335. Further details regarding the results of increasing the control span, i.e. the formation of control band 625, are set forth below.

The increased magnitude of the temperature swings within controlled space 135 due to the increase in the control span are less noticeable to an occupant of controlled space 135 when the occupant is asleep. The increased control span also results in the controlled system turning on and off less frequently and therefore results in less noise disturbance for the occupant. For example, in one embodiment of the invention he increased span results in an average of eight on/off cycles of energy consuming system 125 per hour rather than twelve.

In one preferred embodiment of the invention the temperature setpoint of controlled space 135 can be adjusted according to the circadian rhythm of the occupant as set forth in block 335. For example, it can be assumed that the body temperature of the occupant decreases approximately two degrees Fahrenheit while the occupant is sleeping. Furthermore, it can be assumed that the temperature of controlled space 135 can therefore be lowered by two degrees Fahrenheit without causing any discomfort to the occupant. Execution of sleep determination algorithm 300 then proceeds to exit terminal 340 and terminates. Furthermore, any other operations that can be advantageously performed when the occupant of controlled space 135 is asleep can be performed conditionally in accordance with the determinations of sleep determination algorithm 300.

Figure 4:
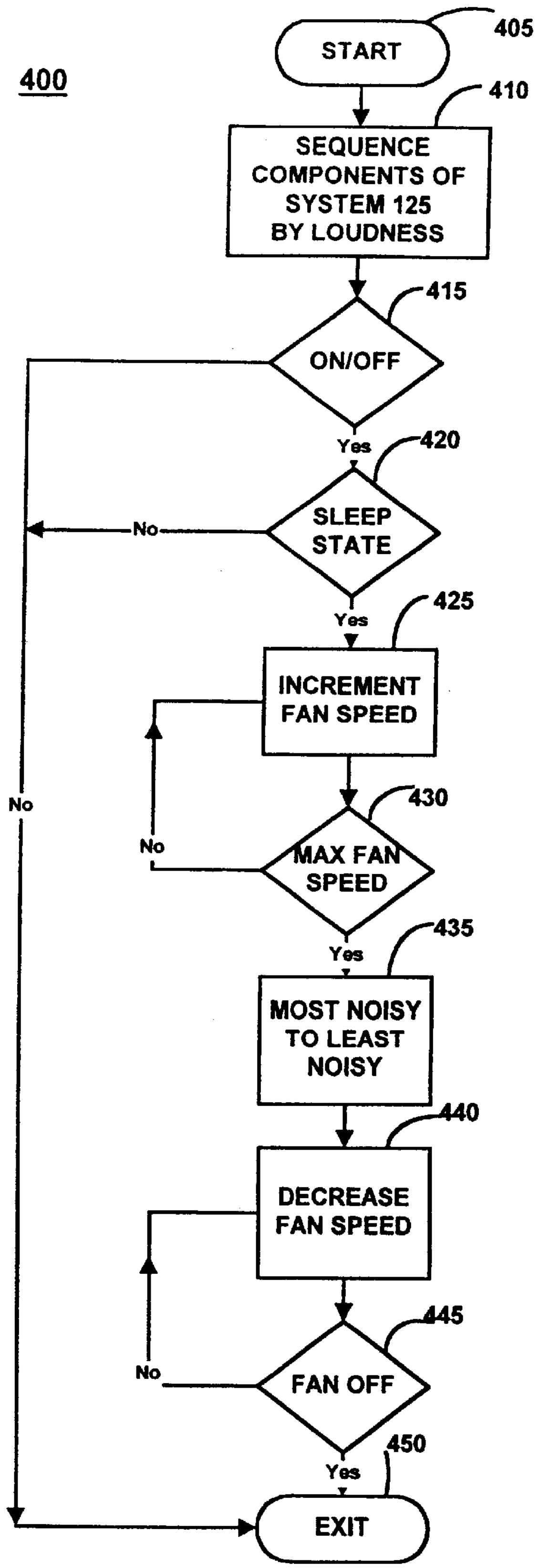
FIG. 4 shows a flow chart representation of an algorithm for reducing noise in the occupied space of FIG. 1 suitable for use with the energy management system of the present invention.

Referring now to FIG. 4, there is shown noise reduction algorithm 400 of the present invention. Noise reduction algorithm 400 can be used to mask the noise produced by energy consuming system 125. Masking the noise in this manner reduces the noise perception of an occupant of controlled space 135. Application of noise reduction algorithm 400 is particularly advantageous when the occupant of controlled space 135 is sleeping because the noise of an HVAC system can disturb the sleep of the occupant if it is not reduced.

Execution of noise reduction algorithm 400 begins at start terminal 405 and proceeds to block 410. In block 410 a determination in made of the noise levels of each of the various components of energy consuming system 125 that must be turned on or off during normal operation. The various components of energy consuming system 125 are then sequentially ordered from the most noisy to the least noisy according to the noise level determination of block 410.

In decision 415 of noise reduction algorithm 400 a determination is made whether energy consuming system 125 is about to be turned on or off. The determination of decision 415 can be affirmative if there is either a transition from the on state to the off state or a transition from the off state to the on state. If the determination of decision 415 is negative execution proceeds to exit terminal 450 and noise reduction algorithm 400 terminates. If the determination of decision 415 is affirmative a determination is made is decision 420 whether the occupant of controlled space 135 is asleep. The determination of decision 420 can be made according to sleep determination algorithm 300. If the occupant of controlled space 135 is not asleep noise reduction algorithm 400 terminates.

If the determination of decision 420 is affirmative one or more of the relatively quiet components of energy consuming system 125 is selected for the purpose of masking the noise transitions of the relatively noisy components. In the preferred embodiment of the invention the fan of a HVAC system is selected as the masking component because the fan is usually the least noisy component of the system.

The energy applied to the selected masking component of energy consuming system 125 can be increased in order to increase the masking noise and therefore increase the effectiveness of noise reduction algorithm 400. In the embodiment where the masking component is a fan with an incremental speed control, the fan speed is gradually increased as show in block 425 and a determination is made in decision 430 whether the fan has reached its maximum speed. If the fan has only discrete speed settings, for example low medium and high settings, the fan speed is advanced through the settings until it reaches the highest one. When the fan reaches its maximum speed execution of noise reduction algorithm 400 proceeds to block 435.

In block 435 operation of the various components of energy consuming system 125 is sequentially terminated starting with the most noisy and proceeding to the least noisy. Thus the noise transitions of the more noisy components are masked by the steady continuing noise of the less noisy ones. In HVAC systems the first component to have its operation terminated is usually the compressor since it is usually the most noisy component in energy consuming system 125. In one embodiment the operation of some rather than all of the components of energy consuming system 125 are staged in accordance with noise reduction algorithm 400. However, in the preferred embodiment all components of energy consuming system 125 can be staged.

After some or all of the remaining components of energy consuming system 125 are sequentially turned on or off in this manner the selected masking component is turned on or off. In the case where a fan with an incremental speed setting is selected to mask the other components the fan speed is gradually decreased as shown in block 440. The decrease in fan speed is continued until the fan is determined to be off in decision 445. Execution of noise reduction algorithm 400 then terminates as shown at exit terminal 450. Thus, energy management system 105 can give priority to occupant comfort rather than strictly controlling to minimize energy usage.

Figure 5:
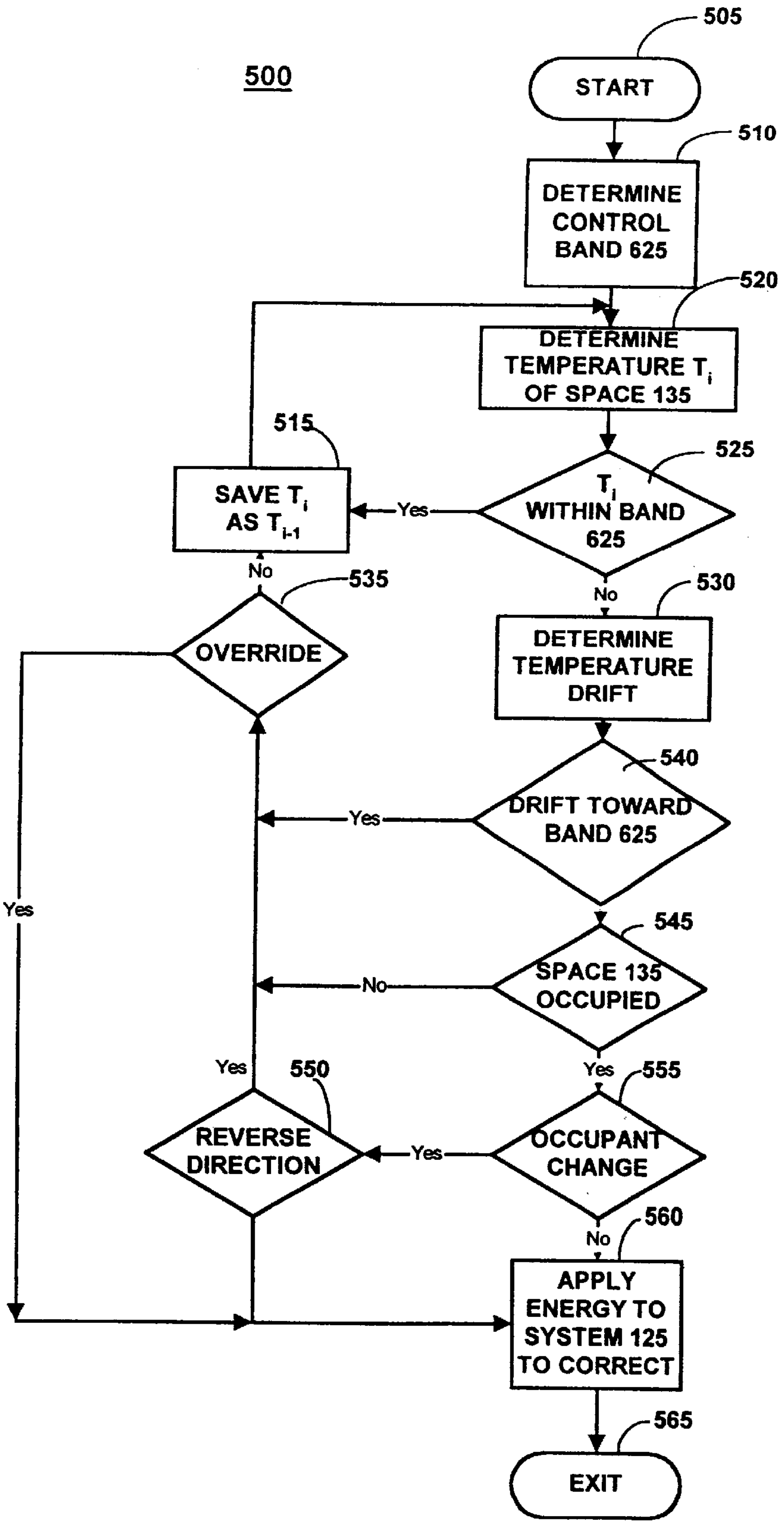
FIG. 5 shows a flow chart representation of an algorithm for controlling temperature drift in the occupied space of FIG. 1 suitable for use with the energy management system of the present invention.
Figure 6:
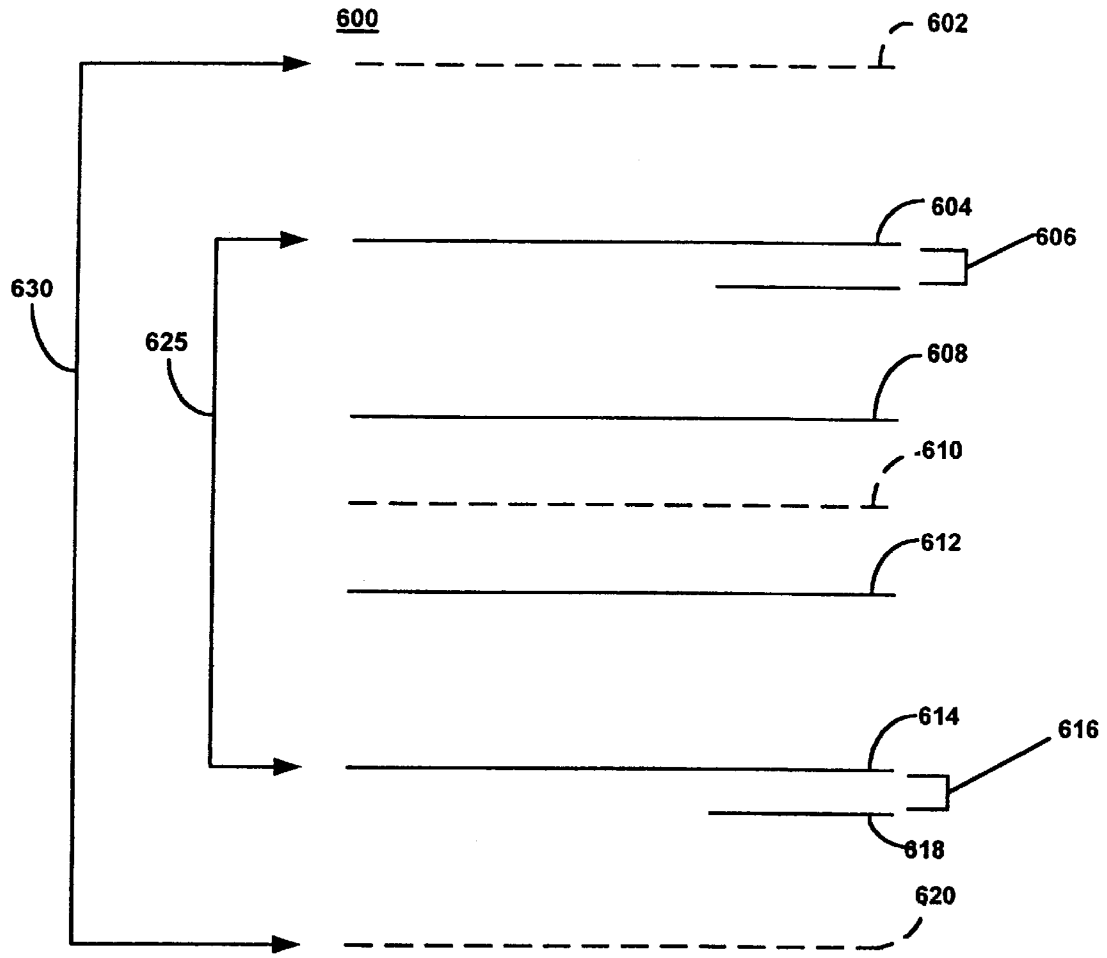
FIG. 6 shows a flow chart representation of various temperature control ranges within the energy management system of the present invention.

Referring now to FIGS. 5 and 6, there are shown parameter drift control algorithm 500 and temperature range chart 600. Parameter drift control algorithm 500 can be used by energy management system 105 to determine the drift direction of parameters of controlled space 135. Temperature range chart 600 shows a plurality of temperature ranges useful for controlling energy consuming system 125 according to the present invention when temperature is the controlled parameter of parameter drift control algorithm 500.

Parameter drift control algorithm 500 can control the return of the temperature of controlled space 135 to a predetermined control band 625 according to the ambient temperature drift of controlled space 135 when temperature is the controlled parameter. The return of the temperature to control band 625 can be implemented either by applying energy to energy consuming system 125 or by inhibiting the application of energy to energy consuming system 125 in accordance with the logic of algorithm 500.

The logic of parameter drift control algorithm 500 begins at start terminal 505 and proceeds to block 510 where control band 625 is determined for controlled space 135. Control band 625 can be determined by the programmer at the time of the programming of energy management system 105. Additionally, it can be determined by the installer at the time of installation. Control band 625 determined in block 510 can be wider than the control span as shown between upper temperature limit 608 and lower temperature limit 612 surrounding temperature setpoint 610. In the preferred embodiment of the invention the control span is within control band 625. Furthermore, in the preferred embodiment a plurality of control bands can be defined. For example, control band 630, including therein control band 625, can be defined and operated upon by temperature drift control algorithm 500 in addition to control band 625.

As shown in block 520 drift control algorithm 500 makes a determination of the current temperature or other parameter of controlled space 135 at time i. In decision 525 a determination is made whether the current temperature is within control band 625 as determined in block 510. If the current temperature is within control band 625 no action is required and therefore no action is taken by energy management system 105. The current temperature of block 520 is saved as a previous temperature in block 515 and a new temperature determination can be made. Sequential temperature determinations in this manner permit a determination of the ambient temperature drift of controlled space 135.

However, if the current temperature of controlled space 135 is not within control band 625 as determined in decision 525 some action by energy management system 105 may be required to return it to control band 625. The determination whether to take some action to return the temperature to control band 625, such as applying energy to energy consuming system 125, can be made in accordance with the logic of parameter drift control algorithm 500 as follows.

A determination of the temperature drift is made as set forth in block 530. The temperature drift within parameter drift control algorithm 500 can be determined using any methods known in the art. For example, the temperature drift can be determined by comparing the current temperature $T_i$ with a previous temperature determination such as $T_{i-x}$ where x is a programmable number of temperature samples. The temperature comparison of block 530 can be used to determine the rate of temperature drift as well as the direction of the drift.

From the rate of drift energy management system 105 can also determine from this information how long it may take for the temperature of controlled space 135 to return to control band 625. In an alternate embodiment of the invention the rate of temperature drift and the time delay before returning to control band 625 can be used to determine whether action is taken by drift control algorithm 500. These determinations, and any other determinations selected by a programmer or an installer of energy management system 105, can be in place of, or in addition to, any determinations set forth herein. Furthermore, using the same principles, the system of the present invention can predict changes in demand for controlled space 135 with respect to lights, hot water, appliances, fireplace or any other parameter obtained by energy management system 105.

A determination is then made in decision 540 whether the temperature drift calculated in block 530 is in the direction required to return the temperature of controlled space 135 to control band 625. If the temperature drift is in the required direction execution of parameter drift control algorithm 500 branches at decision 540. Under these circumstances algorithm 500 may not direct energy management system 105 to apply any energy to energy consuming system 125, even though the temperature of controlled space 135 is not within control band 625. However, as described below, energy may still be applied to energy consuming system 125 if predetermined override conditions are present.

If the temperature of controlled space 135 is not drifting toward control band 625 a determination is made in block 545 whether controlled space 135 is occupied. The determination whether controlled space 135 is occupied can be made by any means known to those skilled in the art. For example, the determination can be made according to ingress/egress information obtained from an electronic lock on a door of controlled space 135. Additionally, the determination can be made according to motion sensors or any other kind of sensors within controlled space 135.

If controlled space 135 is not occupied it may not be necessary to take any action even though the temperature may not be returning to control band 625 or even though it may be returning to control band 625 slowly. Furthermore, energy management system 105 is adapted to permit the programmer or the installer to require any number of further conditions to be met before taking any action. The further conditions can be inserted into parameter drift control algorithm 500 in the vicinity of decision 545 in a manner well understood by those in the art.

A determination is then made in decision 555 whether a change in the setpoint made by an occupant of controlled space 135 is responsible for the temperature of controlled space 135 being outside of control band 625. It will be understood that an out of control band condition can be caused by other factors such as, for example, a change in setback due to time of day or day of week. However, it is important for drift control algorithm 500 to prevent wasteful inadvertent reverses in the direction of control. If a change made by the occupant is determined to be responsible, action can still be taken to apply energy to energy consuming system 125 by drift control algorithm 500. However, under these circumstances action is permitted only if doing so does not require reversing the direction of control, as determined by decision 550. Thus the system is prevented from reversing direction only because of a change in the setpoint.

If the out of control band condition is not caused by the occupant of controlled space 135, or if it was caused by the occupant and it does not require reversing the direction of control, execution of drift control algorithm 500 proceeds to block 560. In block 560 energy is applied to energy consuming system 125 for adjusting the environment of controlled space 135. Thus, energy can be applied as set forth in block 560 in order to return the temperature of controlled space 135 to control band 625.

Those skilled in the art will understand that the temperature control exercised at block 560 is provided with control span hysteresis both at upper limit 604 of control band 625 and at lower limit 614 of control band 625. In the preferred embodiment of the invention control span 606 at the upper lift of control band 625 can be located within control band 625. Control span 616 at the lower limit of control band 625 can be located immediately outside of control band 625. Thus, when the system of the present invention cools controlled space 135 the lower lit of the hysteresis is the lower limit of control band 625. When the system of the present invention heats controlled space 135 the upper limit of the hysteresis is the upper limit of control band 625. This placement of control spans 606, 616 has been determined to save energy compared to the case where control spans 606, 616 are centered around temperature limits 604, 614, respectively.

As previously described, the method of the present invention permits an override of any determinations made within drift control algorithm 500 to prevent activation of energy consuming system 125. Thus, in decision 535 a determination is made whether any of a predetermined set of override conditions is present. The override conditions can be any conditions determined by a programmer or installer. They can include conditions such as how long it may take controlled space 135 to return to control band 625, the time of day, the day of week, the month, the day of the month, the season of the year, ingress and egress, window opening and closing, change in status, occupancy state, the circadian rhythm of occupant, the ambient noise level, the light level, the energy consumption, the temperature drift, the rate of energy consumption, utility tariffs, the humidity, the environment or weather and others.

If none of the override conditions are determined to be present according to decision 535 execution of parameter drift control algorithm 500 does not permit any change in the control of energy consuming system 125. Rather, execution of control algorithm 500 returns to blocks 515, 520 to make a further determination of the temperature or other parameters of controlled space 135. Some of the variables and parameters that can be used by parameter drift control algorithm 500 and by other algorithms and operations in performing the functions of the system and method of the invention are set forth in Appendix II attached hereto.

Other logic and parameters, in addition to those set forth in FIG. 5, can be implemented by the programmer or the installer of the present invention. For example, if controlled space 135 is unoccupied on a weekday it may be desirable to control first at 64 degrees Fahrenheit and then lower the setpoint to 62 degrees after twelve hours of being unoccupied. If controlled space 135 is unoccupied on a weekend it may be desirable to control first at 64 degrees Fahrenheit and then lower the setpoint to 62 degrees after twelve hours of being unoccupied as previously described. However, after the passage of another four hours on a weekend the control temperature can be lowered another four degrees. This saves energy if it is known that occupied space 135 is less likely to be used on a weekend. Furthermore, it will be understood that any temperature settings or time periods for waiting before altering temperature settings can be modified in accordance with any parameter within the system of the present invention.

Figure 7:
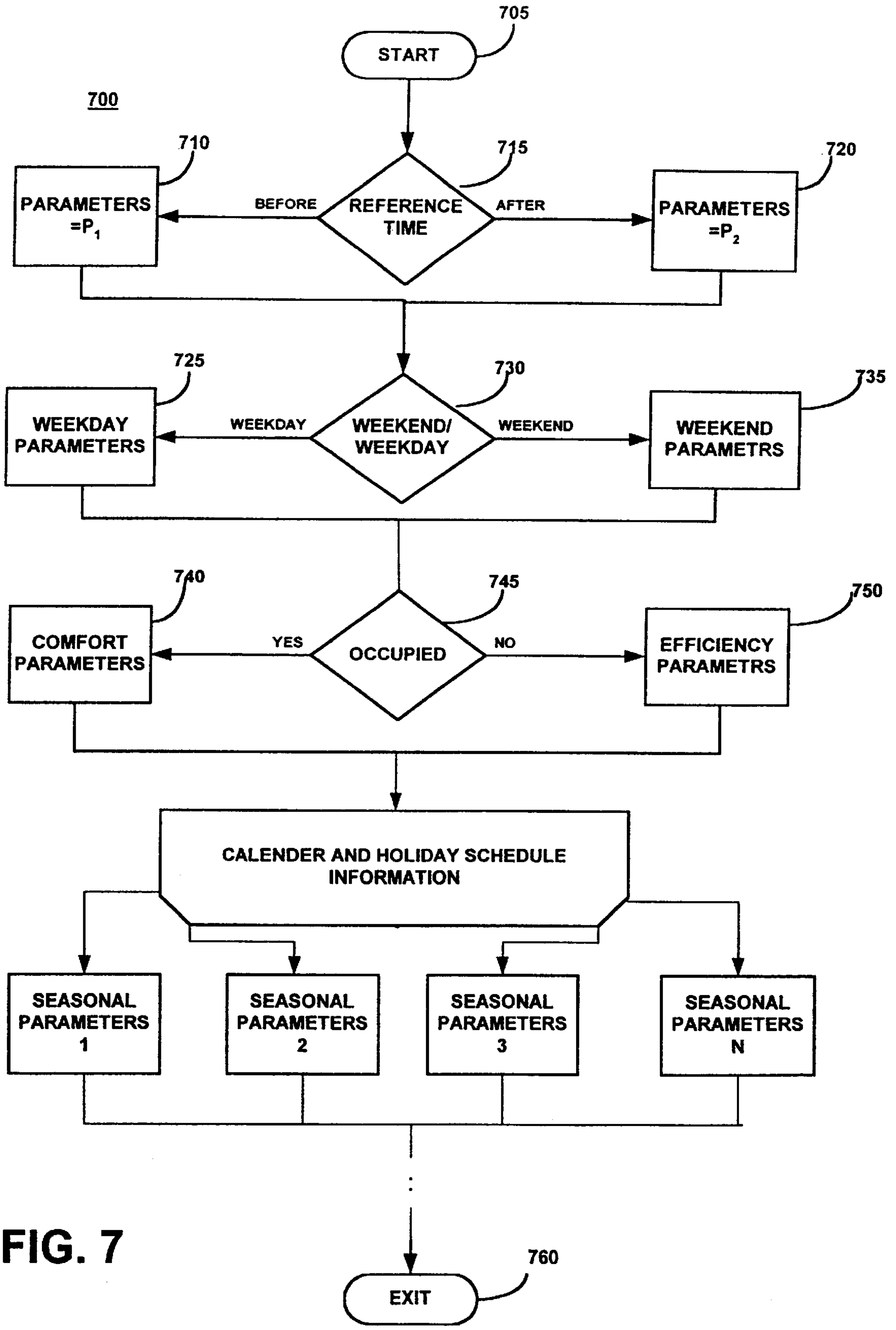
FIG. 7 shows a flow chart representation of a method for using knowledge such as time and calendar knowledge to control the operations of the system of the present invention.

Referring now to FIG. 7, there is shown a flowchart representation of conditional parameter adjustment logic 700 of the present invention. Conditional parameter adjustment logic 700 illustrates the concept that any of the parameters of energy management system 105 can be adjusted dynamically during operation of energy management system 105. Furthermore, the parameters of energy management system 105 can be adjusted in accordance with any conditions available to system 105. Additionally, any parameter within controlled space 135 that can vary over a band of values can be controlled in this manner and drift control algorithm 500 is not limited to the control of temperature. For example, humidity and light within controlled space 135 can be controlled according to parameter drift control algorithm 500.

The conditions available for adjusting parameters within adjustment algorithm 700 can include any programmable conditions and any conditions inputted during installation or operation of energy management system 105 and any of the other parameters set forth in Appendix II. Additionally, the conditions can include calculated conditions and any conditions that can be determined according to knowledge of information such as time, calendar and schedules. The conditions can also include any conditions that can be determined according to information obtained from sensors of any type coupled to energy management system 105, as well as any information available by way of keyboards, telephones, the internet, radio reception, other databases, etc.

Execution of conditional parameter adjustment logic 700 begins at start terminal 705 and determines in decision 715 whether energy management system 105 is performing its operations during the day or during the night. This determination can be made by determining whether the current time of execution of logic 700 is before or after a reference time. The reference time itself can be modified to take on any value in accordance with the method of the invention. Depending on whether operation of logic 700 occurs during the day or during the night either a first set of parameter values or a second set of parameter values suitable for either day or night operation can be selected as shown in blocks 710, 720. The parameter values selected can include values such as the temperature setpoint 610, the span of control between limits 608, 612, the control band 625, time values such as the time until predetermined actions are taken and the time required to determine that an occupant is sleeping, and any other parameters, variables, or constants within the system of the present invention.

Execution can then proceed to decision 730 where a determination is made whether the current time is a weekday or a weekend. Depending on the determination of decision 730 a set of weekday parameter values or a set of weekend parameters can be selected by conditional parameter adjustment logic 700. Furthermore, a determination can be made in decision 745 whether controlled space 135 is occupied. Depending on the determination of decision 745 one of a number of sets of parameter values can be selected by conditional parameter adjustment logic 700 in blocks 740, 750.

A determination can then be made of the current season of the year in decision 752. The system of the present invention can store parameters and variations or modifications of parameters for as many different defined seasons of the year as required. Thus, when a defined season of the year is determined execution of parameter adjustment logic 700 can proceed to a selected block 754*a–n* to adjust parameters according to the determined season.

Execution of parameter adjustment logic 700 can continue in this manner making any number of additional logical decisions and adjusting any number of parameters according to any conditions within the system of the present invention before terminating at exit terminal 760. The parameters that can be adjusted, or used as a basis for conditional adjustment, or can be used as a basis for ignoring the thermostat of controlled space 135, include, but are not limited to, those set forth in Appendices I and II attached hereto.

In another feature of the present invention humidity can be independently controlled in a plurality of controlled spaces 135 of a hotel or similar type of building. This permits optimizing tradeoffs between cooling and dehumidification for each of the controlled spaces 135 in the building rather than on the level of the overall building. Furthermore, the optimization can be performed using standard HVAC equipment.

In each controlled space 135 an air conditioning device is conventionally provided with separate cooling coils and a separately controllable fan. It has been determined that more moisture is removed from the air when the fan is operated at a low speed than when it is operated at a high speed. Thus, in accordance with the present invention the speeds of the individual fans are optimized in order to optimize the air flows over the various coils of the independently controlled spaces 135. Since each fan is controllable in accordance with a separate humidity sensor in its respective controlled space 135, the humidity and cooling of each controlled space 135 can be independently traded off by increasing and decreasing the respective fan speeds. Since, control is exercised according to the humidity sensor it will be understood that the present invention thus provides humidity controlled cooling of controlled spaces 135 and permits either independent optimization of cooling or independent optimization of dehumidification.

For example, the rooms of hotels are normally left in a closed-up state when not occupied. In hot humid climates such as Florida the air conditioners must sometimes be run constantly in order to avoid serious and expensive mildew damage to the rooms. By operating the fans of rooms under these circumstances at a low speed in accordance with the system and method of the present invention the moisture of the rooms can be lowered and mildew can be prevented while obtaining a smaller but still acceptable level of cooling. This can be accomplished without incurring the costs of running the air conditioner in its normal operating mode to prevent the mildew.

Furthermore, the humidity setpoints of this invention can be modified at any time and in accordance with any parameter available to the system and method of the present invention. For example, the humidity set point can be modified according to temperature or temperature changes.

Figure 8:
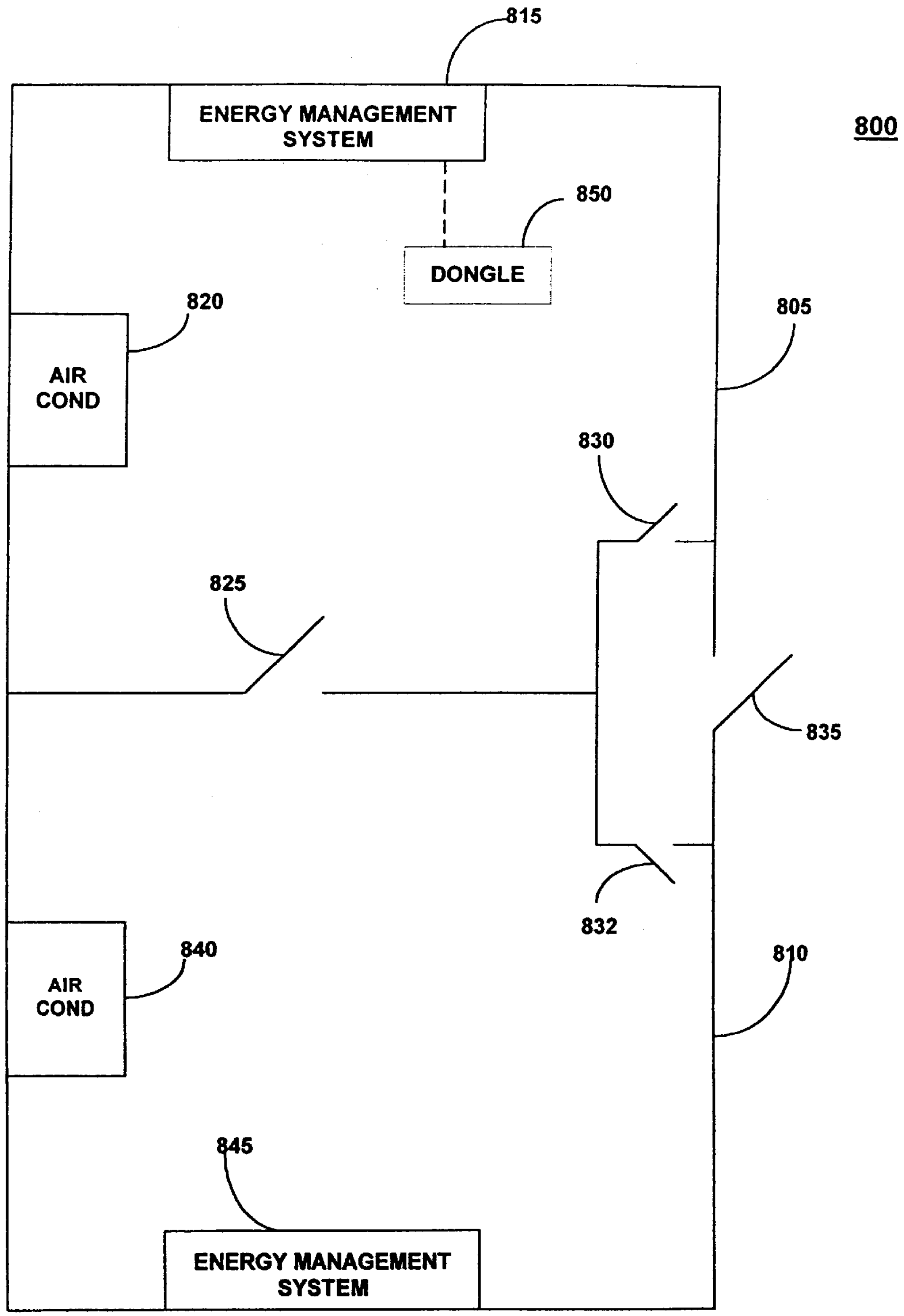
FIG. 8 shows a suite of controlled spaces wherein control can be exercised separately for the individual controlled spaces or over the entire suite as on controlled space.

Referring now to FIG. 8, there is shown controlled suite 800, including controlled spaces 805, 810. The environment within controlled suite 800 can be controlled as two independently controlled spaces 805, 810 or one single large controlled space 800. Thus, controlled space 800 can be operated as two separate rental properties or as one single rental property. Therefore, each controlled space 805, 810 is provided with its own energy consuming system 125 including its own air conditioner 820, 840, its own fan, sensors, and its own energy management system 815, 845. It should be recalled that the amount of distributed processing power physically present within spaces 805, 810 can vary very widely. Ingress and egress, as well as the joining and separating of controlled spaces 815, 845, are controlled using doors 825, 830, 832, and 835.

When controlled spaces 805, 810 are controlled separately energy management systems 815, 845 can operate in a stand alone mode substantially similar to the mode described with respect to energy management system 105 above. When controlled spaces 805, 810 are controlled together as a single controlled suite 800 either energy management system 815 or energy management system 845 can assume control of the entire space and control the environment in a mode substantially similar to the mode described with respect to energy management system 105 above.

In one embodiment of controlled suite 800 the sensors of doors 825, 832, 835 as well as air conditioner 840 can be coupled to energy management system 845. The sensors of doors 825, 830, 835 as well as air conditioner 820 can be coupled to energy management system 815. The controller devices of air conditioners 820, 840 can be coupled to each other and energy management systems 815, 845 can be coupled to each other.

Energy management systems 815, 845, as well as energy management system 105 can be provided with dongle 850. Dongle 850 can include a hardware key to permit selective mating, and thereby electrical coupling, of dongle 850 and the energy management systems of the present invention. When dongle 850 is coupled to an energy management system bidirectional communication of electrical signals is possible between dongle 850 and the coupled energy management system 105.

Thus, any parameters variables or constants within an energy management system can be changed using dongle 850. Furthermore, any such values received by an energy management system 105 can then be used by the system of the present invention to perform any of the operations for controlling energy consuming systems such as energy consuming system 125. Depending on the amount of data and the desired complexity of operation dongle 850 can be a simple logical device or a hand held computer.

Since dongle 850 can receive signals from an energy management system it can receive whatever detailed historical information may be available within the energy management system. The available information can include any information the programmer or installer of the system of the present invention determined should be available. For example, the information obtained in this manner can include how long selected devices operated, how control parameters changed in response to actions of the energy management system or other factors, how long the occupant of controlled space 135 remained in controlled space 135, and how and when the occupant of controlled space 135 changed the settings of the controlled space 135.

The information communicated between dongle 850 and an energy management system can be very useful in individually adjusting parameters and control strategies for a controlled space 135. The adjusted parameters and strategies can then be applied to the energy management system by dongle 850 and used by the energy management system in controlling energy consuming system 125.

The previous description of the preferred embodiments is provided to enable a person skilled in the art to make and use the present invention. The various modifications to these embodiments will be readily apparent to those skilled in the art, and the generic principles defined herein can be applied to other embodiments without the use of the inventive faculty. Thus, the present invention is not intended to be limited to the embodiments shown herein but is to be accorded the widest scope consistent with the principles and novel features disclosed. For example, the present invention can be programmed to maximize use of heat pumps, ambient energy, or geothermal energy without causing discomfort to an occupant of a controlled space. Thus, it can prioritize the use of environmentally available energy such as geothermal or solar energy to increase room temperature or decrease room temperature before using electrical or other non-renewable energy sources. Additionally, it can open and close curtains to assist in heating and cooling controlled spaces. Separate rooms can be controlled separately or as a combined area by the present invention in order provide flexibility in property use. Remote or local control and intervention, including shutdowns, are permitted in order to intelligently manage room loads. Thus, the power company can control the environment within controlled space 135 using the present invention. Control of this nature can permit planned prioritized shut downs during peak periods of peak usage.

APPENDIX I: SOFTWARE FOR OPERATING THE ENERGY MANAGEMENT SYSTEM AND METHOD OF THE PRESENT INVENTION

:08000800F700030E031383123D
:10001000F6000A08F9000C1C3A280C1010100030E9
:100020008E0080308F001014AC0A5D143C302C021E
:1000300031D3A28AC01AD0ADD143C302D02031D2E
:100040003A28AD01AE0A5D1718302E02031D3A287A
:10005000AE01AF0AB00ADD1508302F02031D3328A8
:100060000130AF005D1613303002031D3A28013015
:10007000B0005D1779088A00760E8300F70E770EC0
:1000800009008B138A0182073F3406345B344F34F6
:1000900066346D347D3407347F346F3477347C3488
:1000A00039345E34793471340130230 28B138A0180
:1000B00082076F2C692C4B2C3F2C8B2974287628B7
:1000C0007228E62BF32B622BF32BD52B052C072C58
:1000D0009E2B7A2B632B6B2B932B822B092C0B2CB7
:1000E0008B298B298A1580298A1585298A158929C2
:1000F0008B138A01820700003134383 42E343234B5
:100100008B138A0182074534523452340 0340A3446
:100110000D340034503431340034031383120 8306A
:1001200085000830860038308700 0C1083160B30AD
:1001300085003B30860000308700 9F308100013011
:100140008C00C0308B0083120F30900089309F00EC
:1001500083160430 9F00831283136400 83168E1C61
:10016000B3288312C3288E1083122030840080 01AC
:10017000840A841FB728A03084008001840A031DEC
:10018000BD2831143217A10106263A08B300B31F67
:10019000CF286630A10006263A08C3008716451E00
:1001A000D928C51DD9283216B3133308A200A101DE
:1001B000BB25B224BE2405160515CE240512051153
:1001C0008B13DA268B172230F100C1236030A10097
:1001D00006263A08B3006130A10006263A08E4007A
:1001E000 0130C6000030C7000130C8000030C9002F

:1001F0000130CA000030CB008130CC000030CD008F
:100200008130CE000030CF00A4012E30A500043094
:10021000A6004630A700C425A4013230A500063050
:10022000A6004A30A700C4250230C7000330C8002A
:100230003C30C9009630CA000030CB000230CC0000
:100240000430CD00A4010430A5000730A6004730DB
:10025000A700C4254A30C7004C30C8004E30C90042
:100260005030CA004030CB003E30CC003C30CD0096
:100270003730CE00A4010B30A5000830A60047306F
:10028000A700C4251E30C7000030C8000130C900D7
:100290000430CA000130CB000630CC000230CD0063
:1002A0000130CE00A4011330A5000830A60047306D
:1002B000A700C4250230C7005530C8004430C9002B
:1002C0000130CA004A30CB004430CC000030CD00B1
:1002D000A4011B30A5000730A6004730A700C425A5
:1002E0000A30C7000230C8003730C9000430CA00E5
:1002F0000030A4012A30A5000430A6004730A70032
:10030000C4250317FC3007050313C50003177F300E
:1003100008050313C4008B17321AA629861E9229DA
:100320008A1540290519A6291F151F1995291E0888
:10033000A100943C031CA0297C3021020318A429AD
:1003400031148716B115A62931108712BE01031783
:10035000FC3007050313A10045060319BE29A200BE
:100360003E08031DB7292208BE008B24A7292208B6
:100370003E02031DA6292108C500542BBE01031708
:100380007F3008050313A10044060319D629A200F3
:100390003E08031DCF292208BE008B24BF29220856
:1003A0003E02031DBE292108C400572B5D1C8B296A
:1003B0005D1041080319E029C10BE1290230AA00B0
:1003C0000511831603130B3085003B308600831222
:1003D0008030F1061D25E2018B1316278B1762086A
:1003E000319F529F000E324222AD4080319D40ABA
:1003F0007F305402031CFE297F30D4007F24540830
:1004000080001030A100A201B401000803195408B3
:10041000A2070318B40A7F24A10B052A0430A10007
:100420000310B40CA20CA10B102A2208A000653006

:10043000A10006263A080130A10006263A08200845
:10044000A024E3242230A10006268A150A208A155A
:10045000E7208A156808031D5F208A11AA0803197E
:10046000322AAA03B1183A2A331D3A2A331E8712B8
:10047000331A8716DD1C582ADD10BF08031DBF0381
:10048000BD08031DBD035D10DE0A3C305E02031D86
:10049000582ADE01DF0ADD175D1D582A5D11E00ACA
:1004A000C30AB31F582A4308A2006630A100BB2527
:1004B000311C762AB118722A3F08031D8B29321F7E
:1004C000732A7130A1000626A1015930BA0203181F
:1004D000652ABB03031D652A3A07AC0032130130BD
:1004E000BF008B29BF013110B31F762AB31F862AA4
:1004F000C308031D532BB3133308A200A101BB256E
:100500000430A10006263B1CD52A36243212B3182B
:100510008B2A441AB72A331E8F2A331FD82AAA08D7
:10052000031DD82AB11DB72AB111331E992A441AC6
:10053000D82A1E30A1000626BA080319A52A63305E
:10054000A10006263A08F100AC2A1F30711D2030A8
:10055000A10006263A08C000F116711209302A24BB
:1005600003190230E300DE01DF013624D82A1830F7
:10057000A1006408A1070626BA08031DC32A0F308C
:10058000E4181230BA00B11CC72A0130BA005E0864
:10059000E4185F083A02031DD82AE4080319D52A93
:1005A00003306402031DE40AD72A0D2401307924A4
:1005B000331EDD2AE401F118352B6430331AE62AA4
:1005C000711BE62A0F307118E62A0B30A10064086F
:1005D000A10706263A08643C031CF22A40303A027E
:1005E0000318F62A413071185530F72A3A08E50009
:1005F00007306705031D032B711C012B6308E502FF
:10060000032B6308E507711C1C2B03306739031D9E
:10061000162B6839031D162B650820020318352B8D
:10062000E8168A155F208A11E814322B650820022B
:10063000031C352B6817322B04306739031D2D2B13
:100640006839031D2D2B200865020318352BE81689
:100650008A155F208A116815322B20086502031C59
:10066000352BE8178A155F208A118B29B2240E30AA

:10067000A1000626BA080319522BBB080319522BF6
:10068000B21B522B0000462BB21D4C2BBD08031D84
:10069000522B4F2BB211B2242708BD00522B3A081F
:1006A000BD00B21500008B290D30A300592B053079
:1006B000A300A30ABE0803198B290310BE0C031C58
:1006C000592B5428592B451A592B71117114F110BB
:1006D0001D25D123B72BC51A592B3030F1061D2506
:1006E000D1230330670503 1DB72B711A6816711EDD
:1006F000E816B72BC519592B71157110F1101D256E
:10070000D123B72BC51B592BF1151D25BD238624DD
:100710000317803007050313031DAF2B4008633C0C
:100720000318C00A862B451B592B711171127110C9
:10073000F114F116E8161D25D123B72B4519592BB5
:10074000F1151D25BD23862403170430070503 1367
:100750000031DAF2B293040020318C003A22B8624AF
:10076000F1111D256430A1004008A200BB256330B3
:10077000A1007108A200BB25592BD1234008A02459
:10078000E32C6430A10006263A08643C031CCE2BFF
:1007900027303A02031CCE2B3A08CF2B4630C0003C
:1007A00008000530C100051508001230A10006261A
:1007B0003A08C300C309C30AB317871633134308A3
:1007C000A2001630A100BB253624592BC419ED2BED
:1007D0003110B11C592B8712592BB1153114B11C92
:1007E000592B8716592BB31B592B331BFB2B331754
:1007F000B82500307924331E002CAC01DE01DF0166
:100800000530AA00441E7E24592BB1148B29B11047
:100810008B2931158B2931118B2933123317E001C4
:10082000DE013215B224B8256230A1000626BA08CE
:100830000031D08000A302A2403190530E30046305E
:10084000040020318262C71157110282C7111711497
:100850001D250800A10006263A080319342C0A3C7D
:10086000031C342C3A08080003150800 3316B21193
:100870003211DE01AC01441A3E2C3313B82D043082
:10088000BA003A087820B6009A248A151C218A11E9
:10089000BA0B412C8B290F30B10570303305B104F0
:1008A000B113B11744088A151B218A11043032058F

```
:1008B0003104B31F5C2C0438B6003F080319612CC7
:1008C000B6148A151C218A1120088A151B218A1149
:1008D0008B292408A1002508A200BB258B29240808
:1008E000A10006263A08B6009A248A151C218A110E
:1008F0008B29E400A2006130A100BB2D0800DC0AB6
:100900000F30DC05A0305C07840008008724882 4B1
:10091000FA30F500922C0630F500922C6430922CBF
:100920003230F5009A24F50B922C080020309B2CD5
:100930001A309B2CC730F4006400F40B9C2C080088
:10094000A100A2010A30A102031CA82CA20AA22C19
:100950002107F000A20DA20DA20DA20DF03022057C
:10096000F00408008712331 8BD2CB118BD2CAC015F
:100970002130A10006263A08BF0008000F30900081
:100980003170130 8E0007308D0049308F00900131
:100990009101940195018F17031308000030F000B6
:1009A000E3248E241130F007031CD02C0130F10019
:1009B0001D258E24203087060310F10D031CD82C32
:1009C00087120800F00083120317053090051110FC
:1009D00011107309405151 1F0307005F300F30C78
:1009E000F30CF30CF30C0F3073054120F200721876
:1009F0001416F218151572191115F2199014721AAD
:100A00009015F21A9415721B10160F3070054120C4
:100A1000F20072181417F218941772199017F2193D
:100A20001114721A9016F21A9416721B10170313EF
:100A30008B170800F1171D2DF11303171010101 15B
:100A40009110141094101411151095107118101 5A0
:100A5000F118141571199414F1199514711A91144F
:100A6000F11A1014711B1414F11B15140313080050
:100A7000A3002508B4002408A200E11424082508D6
:100A8000A400FF30A406FF30A3062330B7005F2583
:100A9000071A4D2D87119624071696248715962 43C
:100AA000071296240 8005F25071E592D87119624EA
:100AB000071296248715962407169624080083169 5
:100AC0000030870083129624080083161030870 0B8
:100AD0008312962408005F256E2D65250830B60028
:100AE0003708840096248711962480 0D0318071276
```

```
:100AF000031C071696248715800C9624071A0310EA
:100B0000071E0314800DB60B722D96248316071A48
:100B10009C2D831296248711000000000000065259B
:100B2000611796248715962407 1E611300000000A4
:100B3000871100005F25AF2D831296248711E11FD6
:100B4000A92D962407165F25871596240716962447
:100B5000AF2D07125F259624871596248711E1187B
:100B60000800B40A0319A20A0800E112E115C52D14
:100B70003308A200A1010130A6002208BA003A30D1
:100B8000A700A4012108A500E1115030B8006112AE
:100B90000230B500A0303825611AD42D6B25611FB5
:100BA000DB2D9A24B80BCA2D61162030E11A2130B2
:100BB000E200532508005030B800B70AB50BCC2D21
:100BC000E119042EE1102608B500031DED2D0130BA
:100BD000B5002708A1002130A7006110E113270804
:100BE000B700031DFE2D61142130B700611CFE2DDE
:100BF0008A1593218A118A15F0208A116B25B70A6C
:100C0000B50BF62D53250800E11108000230A600AF
:100C1000A4012108A5003A30A700B5255325A1302D
:100C200038256B252608B5002708B700E1106110AC
:100C3000E113A708031D1F2E2130B7006114B50B67
:100C4000222EE1176D256118272EB70A2C2E2108B8
:100C5000B6008A151C218A11E11F1F2E022E0800E2
:100C60004F1076278611C830D0006400D00B352E87
:100C70007B270C30D0008619422ED00B3B2EE13062
:100C8000E200D42E5330D000861D4A2E6400D00BD3
:100C9000442ED42E0830A1008619462EA10B4C2ECE
:100CA0008619542ED00B502E861576270800333027
:100CB000D1006B2EF030D1006B2E5530D1006B2E51
:100CC000CC30D1006B2EB430D1006B2E4430D1002B
:100CD0006B2EBE30D1000830D0007627861100080
:100CE0000000D10C03187B271E30A100A10B762E2B
:100CF0007B278615D00B6D2E080076278611000005
:100D0000000000004F187B271E30A100A10B862E8B
:100D10007B2786150800CF10861576278611 7B273E
:100D20000000000000000000000008619CF140F3002
```

```
:100D3000A1006400A10B992E080003104F180314A2
:100D4000CE0CCD0CCC0CCB0CCA0CC90CC80CC70CEF
:100D5000C60C080086157627D0014730840050085D
:100D600084070008A2000830BA00A20C4F10031834
:100D70004F147D26BA0BB52ED00A08305002031C42
:100D8000AD2E08000930D0000830D2008B264F105D
:100D9000CF184F149D26D20BC62ED00BC42E0800A0
:100DA000E430D72EE130D72EE330D72EE230F000FA
:100DB000E32487247B279A24861DD22ECF0140303E
:100DC000D20030265A268B264F10CF184F148B2670
:100DD0004F08A1000330A1050319F32E03302102AF
:100DE0000319D62EF72E4F1EF62E4F144F169D26A2
:100DF0007D26D20BE32E63268B264F13CF184F1779
:100E00004827031DD02E70304F1F78306F27CF1A20
:100E10000C2FCF164F1ADF2E3F274808B700802728
:100E2000192FE20131128B26CF1C08006527192FDC
:100E300067278B1330265D26AA266926C2268B17C4
:100E400048270319262FE530E20008000930D000BA
:100E5000D801D7014608D8070318D70AD00B2A2F84
:100E6000D401FF30D600F630D8070318D60A56084A
:100E7000D707D71B3D2FD40A312F2030D407652741
:100E8000412F30265D26AA266626861576270800 7D
:100E9000A2014830D000A026CE130318CE17A1011E
:100EA000A10CA20CA2130318A2172108A206A101EB
:100EB000A21BA1152108A206A101A21B2115210830
:100EC000A206D00B4B2FA20808007030682F783094
:100ED000A500A4010830A6004730A7000D2EA500EC
:100EE000A4010830A6004730A700C42D8316333074
:100EF00086008312080083163B30860083120800A8
:100F00000830DB00DA01D9016400D90B842FDA0B39
:080F1000842FDB0B842F080085
:10100000C730F4006400F40B022808008A11062699
:101010008A15080064000F30B10570303305B10443
:1010200003306739031 9B117031DB113BC013A0826
:10103000B60033203B08B60033200430320531 04BB
:10104000B600B31F242836153F0803192828B61404
```

:10105000033204408B60033202008B60033203C0873
:10106000B600362008003608BC078B135A2008301B
:10107000A2004520B60C4320A20B3A2845205A2056
:1010800000208B17080003185A280F30A10085167E
:101090000330B400B40B4A280000085120330B400BA
:1010A000B40B5028A10B47280A30B400B40B5628C3
:1010B000592808008730B400B40B5C2808002D3094
:1010C000A1000620331ABA0E03303A050319033083
:1010D000BC00E81C8228331E7D282C30A10006208D
:1010E000BA0803197D2840082002031C7D28013E10
:1010F0003A0203187D28E8106814E81C8428BC1CF8
:101100007B285F28681C8B283C185F28E81468102F
:10111000BC1C08005F28681C9128671468103030D8
:10112000D828E81C9728E714E8102E30D828681D26
:101130009D28671568113230D828E81DA828053089
:10114000A10006203A08E900E715E813430D82854
:10115000681EB3280530A10006203A08E90067168A
:1011600068123630D828681FC1280630A100062032
:101170003A08E9003030671C2E306710E71068131A
:10118000E028E81FCC280630A10006203A08E90034
:10119000323067 11E813E028E81E0800E812711ADF
:1011A0008003430E71D3630E7116712E812E028F6
:1011B000A10006203A08E6043B08FF3AE605E728C6
:1011C000A10006203B08E6043A08FF3AE605E61BC4
:1011D000516E61F05127F306605C6218A11080034
:1011E0008B1383163B30860083123113A101283004
:1011F000B400861A0129A10BF928B40BF92831177C
:101200008000830A2001B30A10008291230A100FC
:1012100000929A10B0829861A0314861E0310A208A7
:10122000003191529B50CA20306290318B112031CD2
:10123000B1168B170800B60064008B1383161B30A1
:1012400008600831 20A30A2002829B60C03182A2926
:1012500086122C29861600001230A1002F29A10B1E
:101260002E290000A203FE3022070318252901 3091
:10127000220203192A2983163B30860083120800B4
:1012800093213130BB00F020311B7B29BB0AB11AFE

:101290007B293508B800B51F3112B51B311635084A
:1012A000B900B90E0730B9050F30B805311E6529F0
:1012B000851BB80A380884002030840700008B6006F
:1012C00000201C21B90B59297E29A301851BB80ACE
:1012D000F020BB0A311B7B29BB0AB11A7B293808D5
:1012E000840020308407350880000B90B6729A308E3
:1012F000031D8A1154288F213B081B218A118B2939
:101300008D2134301B218A11592B8D2135301B2121
:1013100083298D2136301B21832907309429003001
:10132000942904309429053 0B40034088A158020AB
:101330008A110038031D9D2908001B21B40A952934
:101340008B13A1012830B400061AAC29A10BA429E3
:10135000B40BA42931170800083 0A2001B30A100EB
:10136000B3291230A100B429A10BB329061A031422
:10137000061E0310A2080319C029B50CA203B12947
:10138000 0318B112031CB1168B170800B6006400D5
:101390003112051931160515002086308400 8B1393
:1013A0000A30A200D629B60C0318D8298010DA29F1
:1013B000801400001230A100DD29A10BDC290000FF
:1013C000A203FE3022070318D32901302202031999
:0A13D000D829311E05118B17080003 :00000001FF

APPENDIX II: PARAMETERS THE ENERGY MANAGEMENT SYSTEM AND METHOD OF THE PRESENT INVENTION

Tc= current temperature setpoint
Tg= Guest setpoint input
Tsh1,Tsh2,Tsh3,...Tshn= high energy saving setpoints
Tsl1,Tsl2,Tsl3,...Tsln= low energy saving setpoints
Tah= hi emergency override temperature
Tal= lo emergency override temperature
s1,s2,s3,...sn = degrees span or hysterysis
T1,T2,T3,...Tn= previous temperature measurements where T1 is most recent
M1,M2,M3,...Mn= time previous motion detection where M1 is most recent
trb= time beginning rest period
tre=time end rest period
Ad= Ambient drift direction
Ac= Ambient drift rate
D1= time door open/closed
D2= time balcony door opened
D3= time other door or window opened
Increase decrease variable
Programming input (enter allowable program fill in of logic, data and assignment)
Temperature limits hi
Temperature limits lo
Temperature hysterysis (spans)
High and low setback temperatures
Sleep temperature set back
Circadian rhythm temperature chart, peak times, peak variances, data table, equations, offsets
Desired action(s) upon door opening and/or closing
Desired action(s) upon motion detected
Time to rest-sleep state
Time to unoccupied
Time to system-reset HVAC
Time of begin hi billing rate
Time of medium billing rate
Time of low billing rate
Compressor protection on/off
Compressor protection time
Compressor protection action (system off or fan on compressor off or electric heat in heat mode)
Heat-pump desired mode - upon change from unoccupied to transient or occupied.
Heat-pump minimum outside run temperature
Temperature outside
Humidity outside
System performance data
Manufacturer and model number (interface connection and relay specification selection)
Output device (back end serial number autoset)
Serial number
Dongal parameters
Channel selection and point by point assignment by output channel number ( i.e. compressor relay, electric heat relay, fan relay, reversing valve, fan speed hi, lights, safe, bar, stove, other)

Door switch lock data

Locked, opening, open, card inserted, card ID data (guest, engineer, housekeeper, manager, other authorized, unauthorized)

Room status: occupied, unoccupied, transient (ingress/egress), unrented, seasonal low-occupancy shut-down (emergency maintenance and mildew relief only) (input via network, dongal, computed time-delay, programmer or key-panel)

Time of refresh cycle, calculate using: relative humidity % @ temperatures (3-5 couples T-R.H. per ASHRAE tables of mildew fungus growth)

Remote control trained data (infrared input per each button on remote) Use to operate system TV display of temperature and other data transmitted via infrared link to TV or cable box, operate all system settings including operate as TV on/off, on/off remote, lights on/off/dim, curtain controls, door lock open by way of electric lock, display door frame security camera on TV display, property security alarm (police panic button), fire alarm Maid call Laundry call Bill quick check out Utility cost data Rate hi Rate medium Rate lo Demand hi Demand medium Demand lo Time-of-day, date, year, holiday, day-of-week Occupancy Motion time lag Occupant class Mode of operation heat cool Light Noise Motion Door motion Door position Time of door opening Temperature Rate and direction of ambient temperature change Circadian rhythm Delta temperature Rate of delta temp Alternate entrance position Window position Optional entrance status Temperature Humidity Outside temperature (other temperatures Outside humidity Solar enthalpy Wind Real time power ( energy) demand Cost of each energy type Curtain position open/closed Temperature behind curtains Occupancy detection Ingress/egress detection Activity detection Sleep detection Energy detection Enthalpy detection
Inputs
Outputs
Network connections
Connection method
Sensors
Other device connections
Communications to other systems and purpose
System efficiency calculations
Filter dirty
Compressor weak
System bypassed
System not working
System coil frozen
System BTU actual
System BTU specification
EER actual
EER calculated
EER specified
Change in EER (efficiency loss)
System vibration
System vibration spectrum change
Noise analysis
Probability of guest returning to room - property based statistics predicting probability of guest entry allowing further setbacks in temperature during low probability times
Utility rate schedule rate changes (according to season, time of day, day of week, holiday, date)
Relative humidity (indoor, outdoor, desired or setpoint value, indoor air quality relative humidity table)
Rental status – rented, unrented, unrented but reserved for rental at date-time, seasonal or periodic (such as weekend) shutdown maximizes setbacks, unrented long term
User input (engineering, installer, and occupant)
Temperature set points (desired by occupant and setbacks)
Desired functional control such as heat, cool, light on/off/dim, service, alarm, emergency heat, TV on/off
Increase decrease variable
Programming input (enter allowable program fill in of logic, data, and assignment)
Occupancy status

- occupant normal
- occupant resting
- occupancy transitional
    - unoccupied to occupied
    - occupied to unoccupied
    - short term resting to long term resting
    - occupancy alert (looking for changes such as ingress/egress)
- occupancy by maintenance
- occupancy by housekeeping
- occupancy bypassed

What is claimed is:

1. A method for managing the energy usage of an energy consuming system adapted to determine the energy of a controlled space, the energy consuming system including a plurality of operating components having on and off states and a plurality of differing noise levels when making transitions between the on and off states, comprising the steps of:

(a) determining the noise levels of the components of the energy consuming system;

(b) selecting a relatively low noise level component of the energy consuming system to provide a selected noise masking component;

(c) causing a relatively high noise level component of the energy consuming system differing from the selected noise masking component to make a transition between on and off states; and (d) causing the selected noise masking component to make a transition between its on and off states after the transition of step (c).

2. The energy management method of claim 1, comprising the step of increasing the noise level of the selected noise masking component prior to the transition of step (c).

3. The energy management method of claim 2, comprising the step of gradually increasing the noise level of the selected noise masking component.

4. The energy management method of claim 1, comprising the step of gradually decreasing the noise level of the selected noise masking component.

5. The energy management method of claim 1, comprising the step of causing a plurality of components to make transitions between their on and off states prior to the transition of the selected noise masking component of step (d).

6. The energy management method of claim 5, comprising the step of causing the components of the energy system to make transitions between on and off states sequentially in accordance with the determination of step (a).

7. The energy management method of claim 1, comprising the step of determining the occupancy of the controlled space.

8. The energy management method of claim 7, comprising the step of performing step (c) in accordance with the occupancy determination.

9. The energy management method of claim 7, comprising the step of determining the occupancy of the controlled space in accordance with motion sensing.

10. The energy management method of claim 7, comprising the step of determining whether an occupant of the controlled space is resting.

11. The energy management method of claim 7, comprising the step of determining the energy of the controlled space in accordance with the circadian rhythm of an occupant of the controlled space.

12. The energy management method of claim 10, comprising the step of determining whether the occupant is resting in accordance with motion sensors.

13. The energy management method of claim 10, comprising the step of performing step (c) only in accordance with the occupant resting determination.

14. The energy management method of claim 10, comprising the step of determining whether the occupant is sleeping.

15. The energy management method of claim 14, comprising the step of determining whether the occupant is sleeping in accordance with time of day information.

16. The energy management method of claim 10, comprising the step of adjusting a span of control of the energy system in accordance with the occupant resting determination.

17. The energy management method of claim 1, wherein the relatively low noise level component of the energy consuming system is the lowest noise level component.

18. The energy management method of claim 17, wherein the lowest noise level component of the energy consuming system is a fan.

19. An energy management system for managing the energy usage of an energy consuming system adapted to determine the energy of a controlled space, the energy consuming system including a plurality of operating components having on and off states and making transitions between the on and off states, comprising:

(a) differing noise levels for the components of the plurality of operating components of the energy consuming system;

(b) a selected noise masking component of the plurality of operating components having a relatively low noise level;

(c) a first system transition between on and off states of a relatively high noise level component of the energy consuming system differing from the selected noise masking component; and (d) a second system transition between on and off states of the selected noise masking component after the first system transition.

20. The energy management system of claim 19, comprising an increase in the noise level of the selected noise masking component prior to the first system transition.

21. The energy management system of claim 20, comprising a gradual increase in the noise level of the selected noise masking component.

22. The energy management system of claim 21, comprising a gradual decrease in the noise level of the selected noise masking component.

23. The energy management system of claim 22, comprising system transitions between the on and off states of a plurality of the components of the energy system sequential in accordance with the differing noise levels.

24. The energy management system of claim 19, wherein the first and second system transitions occur in accordance with the occupancy of the controlled space.

25. The energy management system of claim 24, wherein the occupancy of the controlled space is determined in accordance with motion sensing.

* * * * *